Dec. 15, 1964 P. DOT Plant Pat. 2,462
ROSE PLANT
Filed Sept. 26, 1963
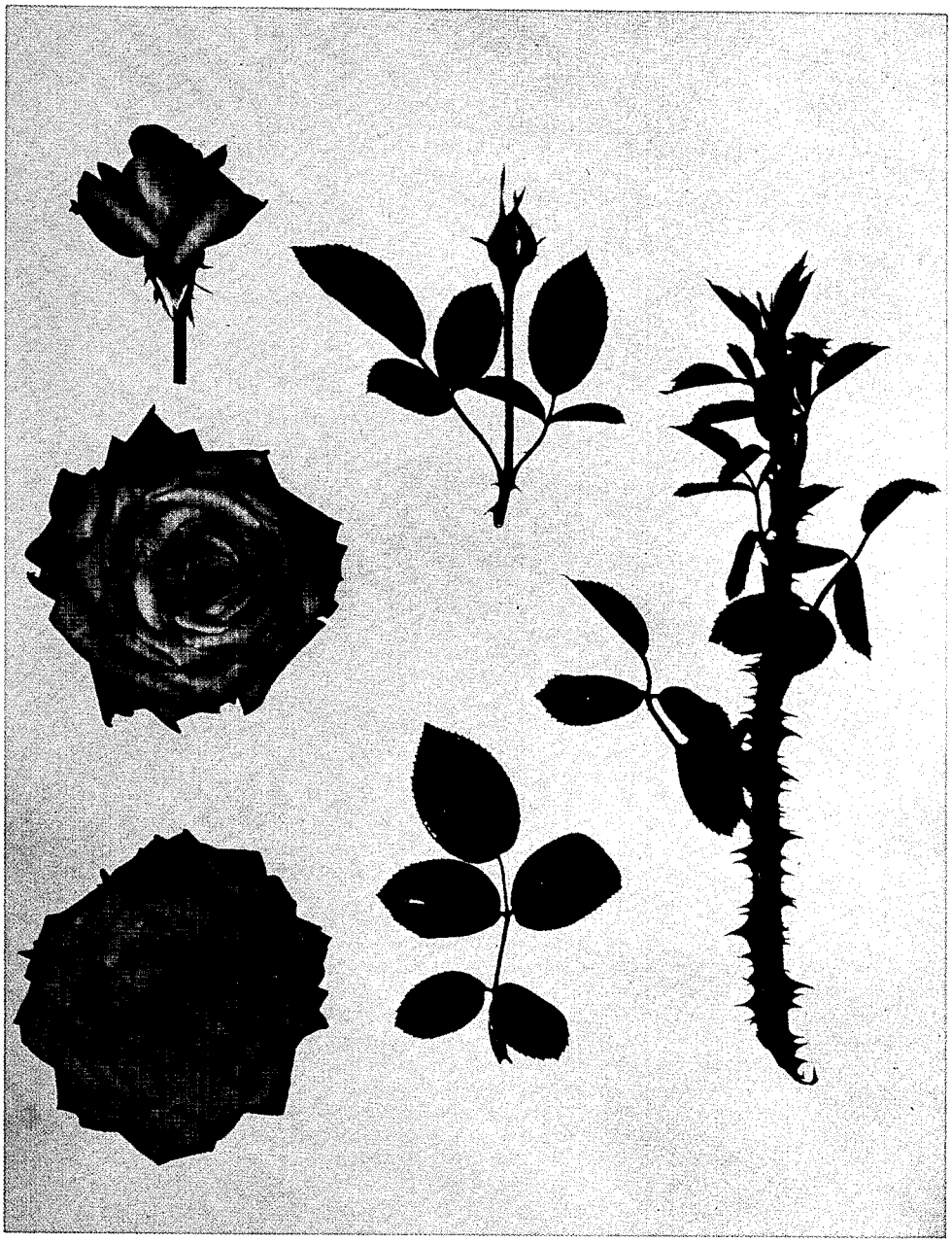
Inventor
Pedro Dot
By: Robb & Robb
Attorneys.

United States Patent Office

Plant Pat. 2,462
Patented Dec. 15, 1964

2,462
ROSE PLANT

Pedro Dot, Barcelona, Spain, assignor to The Conard-Pyle Company, West Grove, Pa., a corporation of Pennsylvania Filed Sept. 26, 1963, Ser. No. 311,930
1 Claim. (Cl. Plt.—20)

The present invention relates to a new and distinct variety of rose plant of the hybrid tea class, which was originated by me by crossing the variety "Baccara" (U.S. Plant Patent No. 1,367) with the variety "Peace" (U.S. Plant Patent No. 591, known in Europe as "Mme. A. Meilland").

As the result of this breeding, I have produced a new and improved rose variety as evidenced by the following unique combination of characteristics which are outstanding therein and which distinguish the same from its parents, as well as from all other varieties of which I am aware:

(1) A tall and upright habit of growth;

(2) A habit of bearing flowers both singly and several to a stem;

(3) The production of blooms of moderate size and having from 50 to 55 petals;

(4) A distinctive and unusual variation in the color of the flower petals due to exposure to sunlight, as evidenced by a change of the dominant Rose Pink color of the open blooms to a Bright Scarlet color;

(5) Very good cut flower longevity, as compared with that of the average garden rose variety; and (6) A slight musk-like fragrance.

In comparison with its seed parent "Baccara," the new variety has better balance in its habit of growth; the flower buds are more pointed; and the flower petalage is considerably less than that of this parent.

As compared with its pollen parent "Peace," the foliage of the new variety is smaller and less leathery; the flowers are also smaller; and the flower color is completely different and bears no resemblance to the flower color of this parent, being from Rose Pink to Scarlet in contrast to the yellow-blushed pink color of the flowers of "Peace."

Asexual reproduction of the new variety by budding, as performed in Spain and at West Grove, Pennsylvania, U.S.A., shows that the aforementioned characteristics and distinctions come true to form and are established and transmitted through succeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Colour Chart of the Royal Horticultural Society, except where general color terms of ordinary dictionary significance are obvious:

Type: Hardy; bush; outdoor; seedling; for garden decoration.

Class: Hybrid tea.

Breeding: Seedling.

*Seed parent.*—"Baccara."

*Pollen parent.*—"Peace" (known in France as "Mme. A. Meilland").

Propagation: Holds its distinguishing characteristics through succeeding propagations by budding.

*Flower*

Locality where grown and observed: West Grove, Pennsylvania, U.S.A.

Flowers borne: Both singly and several to stem; on stems of medium length and normal strength.

Quantity of bloom: From free to abundant, outdoors.

Continuity: Continuous.

Fragrance: Slight. Nature—musk.

Bud:

*Peduncle.*—Long; medium caliper; erect; stiff; medium roughness; with medium number of brown stipitate glands. Color—medium green.

*Before calyx breaks.*—Size—medium. Form—from short to medium length; pointed-ovoid; with foliaceous appendages on the surfaces of the bud; with bristle-like foliaceous parts extending beyond the tip of the bud equal to ¼ or less of its length.

*As calyx breaks.*—Color—Beetroot Purple, Plate 830.

*As first petal opens.*—Size—medium. Form—medium length; ovoid. Color: outside—Rose Red. Plate 724, shaded and partly overlaid with Cardinal Red, Plate 822/1; inside—near Delft Rose, Plate 020/1, often irregularly shaded with scarlet, Plate 19/1.

*Opening.*—Opens up well.

Bloom:

*Size (when fully open).*—Medium; from 3½ inches to 3¾ inches in diameter.

*Petalage.*—Double; from 50 to 55 petals; arranged regularly.

*Form.*—Full at first, but becoming cupped; petals being at first loosely rolled outward and remaining loosely rolled outward at maturity.

Petals:

*Texture.*—Medium thickness.

*Appearance.*—Inside—satiny. Outside—velvety.

*Shape.*—Outer petals—obovate, with apex having one or more notches. Intermediate petals—obovate, and generally having one notch. Inner petals—obovate.

This description of a newly opened flower was made from a rose grown outdoors during the moth of August at West Grove, Pennsylvania, U.S.A.:

*Color.*—Outer petal: outside surface—Rose Madder, Plate 23/1, with base area surrounding point of attachment being tinted with Rose Madder, Plate 23/3; inside surface—Rose Madder, Plate 23/2, becoming Signal Red, Plate 719/3 where exposed to light. Intermediate petal: outside surface—Rose Madder, Plate 23/2 over the central body of the petal, shading to Rose Madder, Plate 23/1 around upper margins and with tinting of Rose Madder, Plate 23/3 surrounding point of attachment; inside surface—Rose Madder, Plate 23/2, with slightly darker shadings on the lateral margins of the petals, and changing sharply to Signal Red, Plate 719/3 where exposed to sunlight. Inner petal: outside surface—Rose Madder, Plate 23/1; inside surface—Claret Rose, Plate 021/1 covering upper half of petals, with lower half being dominated by Carmine, Plate 21/2.

This description was made from a rose that was open for three days outdoors during the month of August at West Grove, Pennsylvania, U.S.A.:

*Color.*—Outer petal: outside surface—Tyrian Rose, Plate 24/2, irregularly shading with Rose Madder, Plate 23/1; inside surface—Carmine Rose, Plate 621/2 covering main body of petals, becoming sharply overlaid with Signal Red, Plate 719/3 where exposed to sunlight. Inner petal: outside surface—Rose Madder, Plate 23/1; inside surface—Carmine Rose, Plate 621/2, with a small area of Carmine, Plate 21/2 surrounding point of attachment.

*General color effect.*—Newly opened flower—Signal Red, Plate 719/3, somewhat reduced in intensity by overlying tints of Crimson, Plate 22/2, with general color effect in cloudy weather being dominantly Rose Madder, Plate 23/2. Three days open—Signal Red, Plate 719/2, overlying Crimson, Plate 22/2.

*Behavior.*—Drop off cleanly; affected by hot, dry, sunny weather by intensification of the Scarlet coloration which can be absent in the opening stages in dull, cloudy weather.

*Flower longevity.*—On bush in garden—3 days in August. Cut roses grown outdoors and kept at living room temperatures—5 days in August.

*Reproductive Organs*

Stamens: Many; arranged regularly about pistils; mixed with petaloids.

Filaments: Many; medium length; most with anthers. Color—near Rose Opal, Plate 022.

Anthers: All open at once; medium size; occasionally an anther fused with a petaloid. Color—yellow.

Pollen: Moderate quantity. Color—gold.

Pistils: Many.

Styles: Uneven; medium length; thin; bunched.

Stigma: Color—yellow.

Ovaries: Some protruding from receptacle.

Hips: None observed.

Sepals: Permanent; moderately long; spear-shaped.

Seeds: None observed.

*Plant*

Foliage:

*Leaves.*—Usually compound of 5 leaflets; normal abundance; moderately large; leathery; dull.

*Leaflets.*—Shape—oval. Apex—acute. Base—obtuse. Margin—irregularly serate.

*Color.*—Mature: upper surface—near Spinach Green, Plate 0960; under surface—Lavender Green, Plate 000761. Young: upper surface—Spinach Green, Plate 0960, heavily overlaid with Maroon, Plate 1030; under surface—somewhat darker than Erythrite Red, Plate 0027.

*Rachis (the supporting stem of the compond leaf).*—Medium caliper. Upper side—grooved; hairy. Under side—sparsely prickly.

*Stipules.*—Moderately long; narrow; with moderately long points turning out at an angle of more than 45°.

*Disease resistance.*—Comparable to that of the average rose variety grown under the same cultural conditions at West Grove, Pennsylvania, U.S.A.

Growth:

*Habit.*—Bushy; upright; much-branched.

*Growth.*—Free.

*Canes.*—Medium caliper.

*Main stems.*—Dull. Color—Spinach Green, Plate 0960/1. Prickles — several; medium length; hooked downward; color—brown. Hairs—none.

*Branches.*—Dull. Color—Spinach Green, Plate 0960. Prickles—many; varying lengths; hooked downward; color—greenish brown. Hairs—few; color—brown.

*New shoots.*—Dull. Color—green, overlaid with purple. Prickles — many; hooked downward; color—reddish purple. Hairs—several; color—reddish purple.

I claim:

A new and distinct variety of rose plant of the hybrid tea class, substantially as herein shown and described, characterized particularly as to novelty by the unique combination of a tall and upright habit of growth, a habit of bearing flowers both singly and several to a stem, said flowers being of moderate size and having good petalage, a distinctive and attractive general color tonality of the flowers, said color being dominantly Rose Pink in the open bloom stage and changing to a Bright Scarlet due to exposure to sunlight, good cut flower longevity, and a slight musk like fragrance of the flowers.

No references cited.